United States Patent [19]
Perler

[11] Patent Number: 4,863,072
[45] Date of Patent: Sep. 5, 1989

[54] SINGLE HAND OPERABLE DENTAL COMPOSITE PACKAGE

[76] Inventor: Robert Perler, 25 Lockwood Ave., New Rochelle, N.Y. 10801

[21] Appl. No.: 86,705

[22] Filed: Aug. 18, 1987

[51] Int. Cl.⁴ .............................................. B67D 5/42
[52] U.S. Cl. ..................... 222/390; 433/90; 433/82; 433/89; 604/224; 604/227; 604/228; 604/222; 604/311
[58] Field of Search ............... 222/390, 323, 465.1, 222/342, 191; 433/90, 89, 82, 81, 80; 604/224, 222, 227, 228, 218, 311, 38

[56] References Cited

U.S. PATENT DOCUMENTS

| | | | |
|---|---|---|---|
| 1,453,418 | 5/1923 | Tessmer | 604/222 |
| 2,165,597 | 7/1939 | Widoe, Sr. | 222/390 X |
| 2,505,028 | 4/1950 | Boeger | 433/90 |
| 4,005,699 | 2/1977 | Bucalo | 604/224 X |
| 4,121,587 | 10/1978 | Kronman et al. | 604/224 |
| 4,492,576 | 1/1985 | Dragan | 433/90 |
| 4,560,352 | 12/1985 | Neumeister et al. | 222/390 X |

FOREIGN PATENT DOCUMENTS 1364845  5/1964  France ................................. 433/90

Primary Examiner—Joseph J. Rolla
Assistant Examiner—David H. Bollinger
Attorney, Agent, or Firm—Handal & Morofsky

[57] ABSTRACT

Apparatus for the delivery of light-curable composite dental filling material comprises a tubular composite reservoir, plunger and slider. The slider is free to move longitudinally along the reservoir but is matingly mounted to facets on the outside surface of the reservoir to prevent angular movement of the slider relative to the reservoir. The plunger consists of a shaft threaded to mate with the threaded inside diameter of the composite reservoir. The plunger also has a disk integrally formed to end of the shaft at one end and a male front piece at the other. The male front piece mates with a female fitting of a separate composite extrusion element.

9 Claims, 2 Drawing Sheets

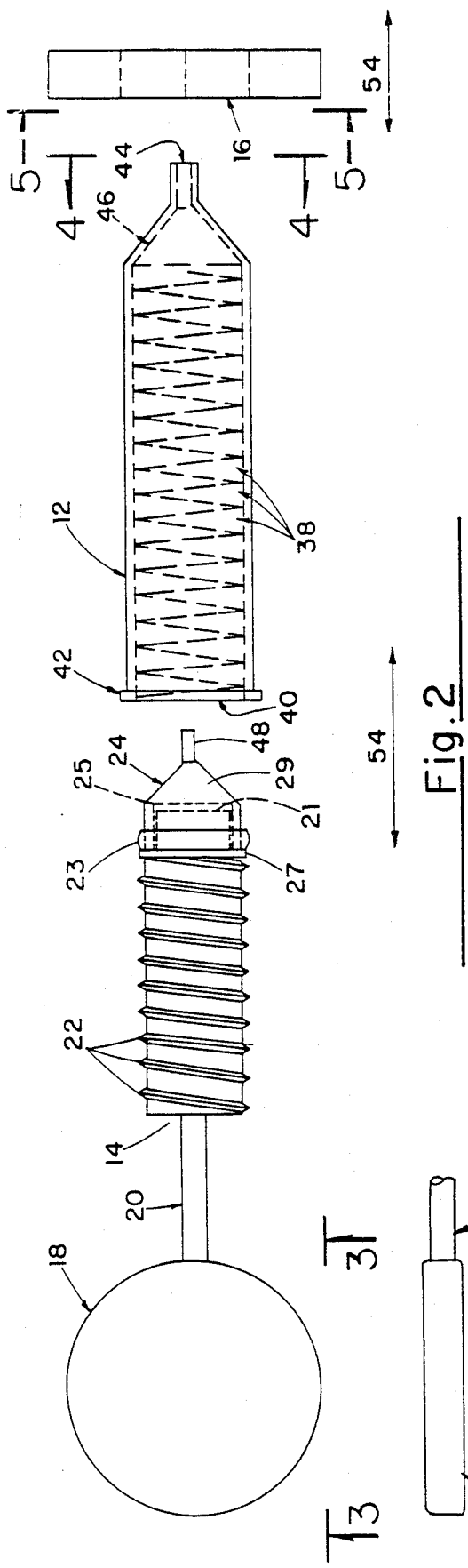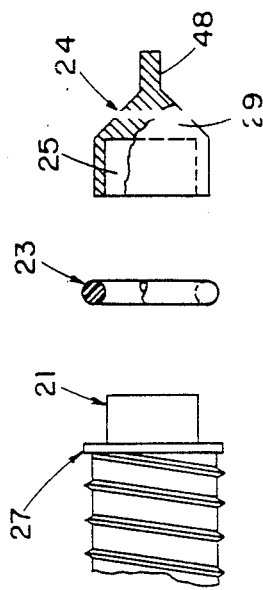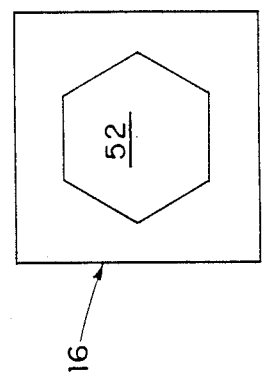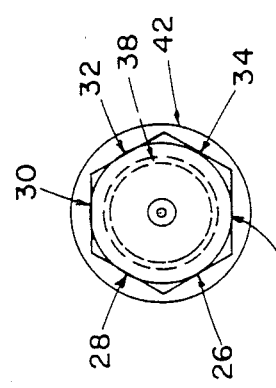

SINGLE HAND OPERABLE DENTAL COMPOSITE PACKAGE

TECHNICAL FIELD

The present invention relates to a method and apparatus for delivering relatively low viscosity, photo-curable composite dental filling material to a convenient site for use in filling a dental cavity.

BACKGROUND OF THE INVENTION

The oldest cavity filling materials presently being used are the "silver" fillings which are made by mixing a powdered metal with mercury to form a metallic material. This material remains formable and can be easily worked to fill a cavity drilled in a tooth by a dentist before permanently hardening. Generally, such materials are relatively easy to work with even without assistance to the dentist from another person. A dentist can use his spatula to take a quantity of powdered metal and mix it with mercury to form a relatively hard, rigid mixture. This material may be loaded into an applicator which includes a cylindrical chamber and a plunger for depositing the material into a cavity in a tooth which has been drilled.

Because of the nature of alloy filling materials, they are easily formulated and loaded into the applicator using only one hand. Likewise, once loaded into the applicator, the material may be applied to the cavity to be filled using a single hand. This leaves the other hand of the dentist free to retract the surrounding tissues as well as keep the field clear of saliva and other extraneous materials which otherwise may introduce impurities into the filling, changing its mechanical and physical properties. Thus the dentist is able to simultaneously prepare and apply filling material with one hand while keeping the field clear with the other.

Recent years have seen a dramatic increase in the use of light-curable composite filling material. These filling materials, typically comprising silica or quartz mixed in a resin base, are typically sold to dentists in the form of tubes or screw and thread syringes. The composite materials used to fill cavities in the posterior teeth must withstand greater compressive force as compared to front teeth fillings. Composite filling materials used for posterior filling require greater compressive strength and are therefore more highly filled. This decreases their viscosity making necessary a greater mechanical advantage in order to dispense.

As discussed above, prior art dental materials such as alloy or silver are made from relatively soft and workable materials which are loaded into an applicator and combine to over time form a permanently hardened filling. In contrast, because modern light-cured composite material must be prepared and packaged in their final form and as such are of relatively low viscosity it is necessary to use two hands to force the material from the tube. Likewise, in the case of screw type syringe packages, the syringe must be operated by rotation of the plunger within the syringe cylinder. Rotation is necessary because of the relatively non-viscous nature of the composite material and the force which must be exerted in order to force it from the syringe cylinder. In particular, the mechanical advantage provided by the screw and thread operation of the syringe results in generating relatively great pressure, thus forcing a relatively hard and non-viscous material out from the syringe. Nevertheless, despite the mechanical advantage provided by the screw and thread of the syringe it is necessary to use two hands in order to force the same to turn and to advance composite material from the syringe.

In view of these limitations, it is customary for the dentist to have an assistant who operates the syringe while the dentist keeps the field clear with his hands. After a sufficient amount of material has been extruded by the assistant, the dentist may take the material from a place where it has been deposited (or directly from the syringe), using, for example, a spatula or the like.

As can be seen from the above discussion, it is thus necessary to have twice the manpower present when the composite material is to be introduced into the drilled out cavity. Clearly the same involves additional cost.

While the composite materials presently being used thus offer many advantages, they suffer from the drawback of being relatively inconvenient to use and expensive in terms of the labor required.

SUMMARY OF THE INVENTION

The invention, as claimed, is intended to provide a remedy. It solves the problem of providing a convenient package for the marketing, storage, and dispensing of composite material. A syringe, adapted for use using a single hand, comprises a threaded cylinder which contains composite material to be fed through an opening located opposite a threaded mating plunger which extends from the inside of the cylinder. A slidable but angularly locked member is provided for securely gripping the composite containing cylinder while changing the angular position of the plunger to advance it through the cylinder. At the same time a constant distance is maintained between gripping surfaces provided on the slider and the end of the plunger allowing it to be operated conveniently using only one hand.

The plunger shaft is terminated by a male front piece which mates with a corresponding female fitting of a separate composite extrusion element. The front male piece passes through an O-ring which sits against the edge of the threaded shaft and thus advances with the plunger as the composite material is advanced, but is not retracted with the plunger if the plunger is reverse screwed. The male front piece mates with the female fitting of the composite extrusion element and thus urges the composite extrusion element forward as the plunger shaft is screwed forward. The male front piece and thus the plunger are free to rotate or slide within the tube relative to the composite extrusion element and as with the O-ring, the composite extrusion element will not be retracted with the plunger shaft should the plunger be reverse screwed. The purposes of this two piece element are as follows; to prevent churning of the composite material, to allow for complete emptying of the syringe, and to prevent reuse of the syringe by reverse screwing and retraction of the plunger. The male front piece is free to rotate and separate from the composite extrusion element and thus no vacuum can be created to suck material into the cylinder through the dispensing end and contaminate the composite material.

BRIEF DESCRIPTION OF THE DRAWINGS

One way of carrying out the invention is described in detail below with reference to drawings which illustrate only one specific embodiment, in which:

FIG. 2 is a partially exploded plan view of the inventive device;

FIG. 3 is a view along lines 3—3 of FIG. 2 illustrating a part of the plunger of the inventive device;

FIG. 4 is a view along lines 4—4 of FIG. 2 illustrating the construction of the composite filling material containing cylinder;

FIG. 5 is a view along lines 5—5 of FIG. 2 illustrating the construction of the slider;

FIG. 6 is an exploded view of the male front piece-O-ring-composite extrusion element system.

DETAILED DESCRIPTION OF THE DRAWINGS

Figure 1:
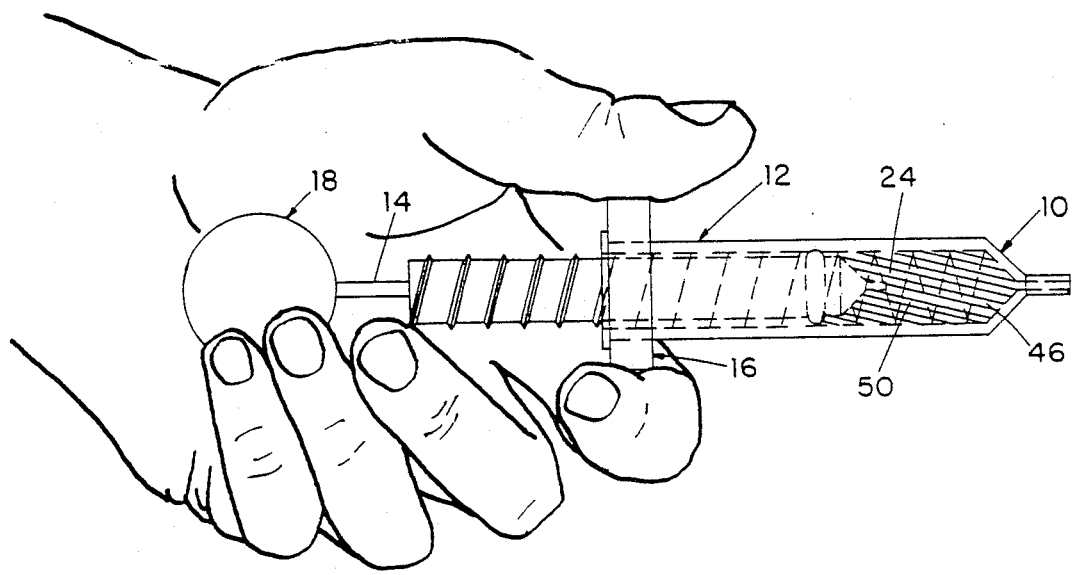
FIG. 1 is a perspective view of the inventive composite delivery system in use with the syringe full of composite dental filling material.

Referring to FIG. 1, a composite delivering syringe 10 constructed as in accordance with the present invention is illustrated. As shown in FIG. 2, syringe 10 comprises a tube or cylinder 12, a plunger 14, and slider 16.

As illustrated in FIGS. 2 and 3, plunger 14 includes a disc-shaped end portion 18 which is formed integrally with a shank 20 having threads 22 formed therein. Composite extrusion element 29 and O-ring 23 insure that all of the composite material advances forward as the device is operated. Disk 18 has a diameter on the order of about 4 centimeters.

As illustrated in FIGS. 2 and 4, cylinder 12 has a faceted external cross section forming, in the illustrated embodiment, six facets 26, 28, 30, 32, 34, and 36. The inner surface of the cylinder is circular with threads 38 defined thereby. Threads 38 in cylinder 12 mate with threads 22 on plunger 14. Cylinder 12 is terminated at one end by an open port 40 having an annular bead 42 and is terminated at the other end by a feeder nozzle 44 having a surface 46 which conforms to surface 24 on composite extrusion element 29. It is noted that composite extrusion element 29 has a cylindrical surface 48 which exactly fits in the forward portion of nozzle 44.

As shown in FIG. 5, slider 16 has a hole 52 which mates with the outside surface of cylinder 12 defined in FIG. 4 by facets 26, 28, 30, 32, 34, and 36. Thus slider 16 is free to move along the body of cylinder 12 in the direction indicated in FIG. 2 by arrow 54 but is constrained from angular rotation with respect to cylinder 12.

During use, plunger 14 is positioned within cylinder 12 in the position illustrated in solid and phantom lines in FIG. 1. The space between surface 24 and mating surface 46 is filled with light-curable composite dental filling material 50.

FIG. 6 is an exploded view of the male front piece-O-ring-composite extrusion element system. O-ring 23 fits around male front piece 21 and sits up against edge of plunger shaft 27. Thus, O-ring 23 can only be urged forward by the edge of plunger shaft 27 and will not be retracted should the plunger be reverse screwed. Male front piece 21 mates with female fitting 25 of composite extrusion element 29. Male front piece 21 and thus the plunger 14 are free to rotate and slide relative to composite extrusion element 29. Thus, the composite extrusion element 29 will only be advanced by the forward action of the plunger 14 and will not be retracted with the plunger 14 should the shaft be reverse screwed.

When it is desired to use the inventive package, the syringe 10 is firmly grasped in the hand of the dentist. The pad of the thumb and the side of the index finger are used to rotate slider 16, while the remaining fingers securely grasp disk 18, thus resulting in relative angular movement between the plunger 14 and the cylinder 12. The necessary leverage is provided by making slider 16 with a length of approximately 4 centimeters.

Unlike prior art syringes, the large slider 16 and disk 18 provide a degree of leverage and control which allows the dentist to single handedly advance the composite material through nozzle 44 despite the low viscosity and relative hardness of the material.

Figure 7:
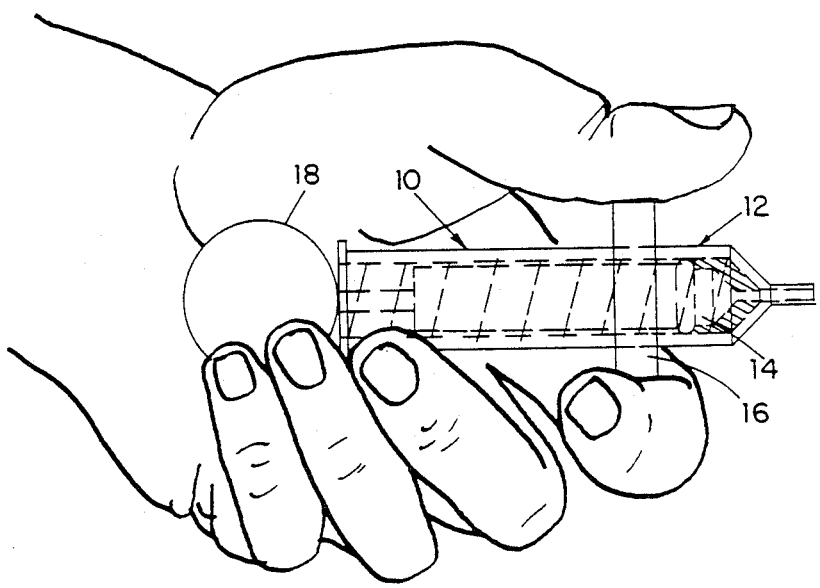
FIG. 7 is a view similar to FIG. 1 showing the operation of the inventive device after almost all of the composite filling material has been expelled.

In addition, the distance between disk 18 and slider 16 can be maintained at a constant value regardless of the longitudinal position of the plunger 14 relative to the cylinder 12. Because this distance can be kept constant, it can be maintained in a position which allows the dentist to apply his maximum strength to the device. Thus, as illustrated in FIG. 7, even when the plunger 14 is advanced into cylinder 12 as far as it will go, the slider 16 allows the distance between the disc 18 and the plunger 14 to be maintained at the same value as when the syringe 10 is full. The use of the slider 16 also allows the syringe 10 to fit any size hand or accommodate any positional preference of the dentist using the device.

While an illustrative embodiment of the invention has been described, it is, of course, understood that various modifications will be obvious to those of ordinary skill in the art. Such changes and modifications are within the scope of the invention which is limited and defined only by the appended claims.

I claim:

1. A dispenser for feeding composite dental filling material, comprising:
   (a) a tube having an inside surface defining an inside volume for containing dental filling material and an outside tube surface of constant cross section along its length;
   (b) threads disposed on the inside surface of said tube;
   (c) a slider with an inside slider surface engaging said outside tube surface and slidably mounted for movement longitudinally along the length of said tube, said outside tube surface being configured and dimensioned to allow longitudinal movement without allowing angular rotation said slider being disposed around said tube;
   (d) a plunger positioned in said tube and configured and dimensioned to be rotatably advanced through said tube;
   (e) thread means disposed on the outside surface of said plunger, said thread means mating with the threads on the inside of said tube; and
   (f) handle means disposed at the end of said plunger opposite the end of the plunger which is disposed in said tube where rotation of said handle means relative to said tube by rotating said slider advances said plunger, said slider sliding to maintain a substantially constant distance between the slider and the handle means as the plunger is advanced.

2. A dispenser as in claim 1 wherein an inside surface of said slider conforms to an outside surface of said tube.

3. A dispenser as in claim 2 wherein said inside surface of said slider has a facet.

4. A dispenser as in claim 1, wherein said plunger is terminated by a front male piece which matingly engages a separate composite extrusion element defined anteriorly by a composite advancing surface and posteriorly by a female fitting, said female fitting correspondingly shaped to accept said front male piece.

5. A dispenser as in claim 4, further comprising an O-ring disposed around said front male piece and said separate composite extrusion element.

6. A device as in claim 1, wherein said handle means is a flat substantially planar member disposed in a plane parallel to the longitudinal axis of said tube.

7. A device as in claim 1, further comprising a nozzle at the end of said tube opposite said plunger.

8. A device as in claim 1, further comprising a mixture incorporating light-curable composite materials.

9. A dispenser for feeding composite dental filling material, comprising:
   (a) a tube having an inside surface defining an inside volume for containing dental filling material;
   (b) threads disposed on the inside surface of said tube;
   (c) a plunger positioned in said tube and configured and dimensioned to be rotatably advanced through said tube;
   (d) thread means disposed on the outside surface of said plunger, said thread means mating with the threads on the inside of said tube;
   (e) flat planar handle means disposed substantially in a plane parallel to the axis of said tube and positioned at the end of said plunger opposite the end of the plunger which is disposed in said tube; and
   (f) slidable gripping means for rotating said tube with respect to said plunger while maintaining a distance between the gripping means and said handle means to accommodate rotation of the gripping means by fingers of one hand of the user while allowing other fingers of said one hand to grip said handle means whereby such rotation advances said plunger.

* * * * *